United States Patent
Krahn et al.

(10) Patent No.: US 10,036,787 B2
(45) Date of Patent: Jul. 31, 2018

(54) MICROWAVE RESONATOR WITH DISTRIBUTED BRAGG REFLECTOR (=DBR)

(71) Applicant: BRUKER BIOSPIN GMBH, Rheinstetten (DE)

(72) Inventors: Alexander Krahn, Karlsruhe (DE); Frank Engelke, Rheinstetten (DE)

(73) Assignee: Bruker BioSpin GmbH, Rheinstetten (DE)

(*) Notice: Subject to any disclaimer, the term of this patent is extended or adjusted under 35 U.S.C. 154(b) by 376 days.

(21) Appl. No.: 14/905,968

(22) PCT Filed: Jul. 9, 2014

(86) PCT No.: PCT/EP2014/064747
§ 371 (c)(1),
(2) Date: Jan. 19, 2016

(87) PCT Pub. No.: WO2015/014586
PCT Pub. Date: Feb. 5, 2015

(65) Prior Publication Data
US 2016/0161576 A1   Jun. 9, 2016

(30) Foreign Application Priority Data
Jul. 30, 2013 (DE) .................. 10 2013 214 930

(51) Int. Cl.
*G01R 33/34* (2006.01)
*G01R 33/28* (2006.01)
(Continued)

(52) U.S. Cl.
CPC ........... *G01R 33/34* (2013.01); *G01R 33/282* (2013.01); *G01R 33/345* (2013.01); *G01R 33/62* (2013.01); *G01N 24/12* (2013.01)

(58) Field of Classification Search
CPC .... G01R 33/34; G01R 33/282; G01R 33/345; G01R 33/62; G01N 24/12
See application file for complete search history.

(56) References Cited

U.S. PATENT DOCUMENTS 9,335,273 B2 * 5/2016 Botto .................. G01N 21/85
9,857,509 B2 * 1/2018 Abdo .................. G02B 5/208
(Continued)

FOREIGN PATENT DOCUMENTS

DE    10 2006 056 064    5/2008
WO    WO 2013/164627     11/2013

OTHER PUBLICATIONS

M. Nakayama et al., "Millimeter and Submillimeter Wave Quasi-optical . . . ", Proc. Sec. Int. Symp. Space Tera. Tech, Feb. 26-28, 1991, Cal. Inst. Tech., 187-190.
(Continued)

*Primary Examiner* — Gregory H Curran
(74) *Attorney, Agent, or Firm* — Paul Vincent (57) ABSTRACT

An NMR (nuclear magnetic resonance) probe head has a microwave resonator with at least two elements which are reflective in the microwave range, at least one of which is focusing. The reflective elements at least partly delimit a resonance volume of the microwave resonator. At least one of the reflective elements is a DBR ("Distributed Bragg Reflector"), and the NMR probe head has at least one NMR coil integrated into the DBR. The NMR detection coil can thereby be positioned particularly near to the sample and the distortions of the static field by resonator components are reduced, such that the detection sensitivity and the spectral resolution of the experiment are significantly improved.

17 Claims, 6 Drawing Sheets

(51) Int. Cl.
    *G01R 33/345*    (2006.01)
    *G01R 33/62*    (2006.01)
    *G01N 24/12*    (2006.01)

(56) References Cited

U.S. PATENT DOCUMENTS

2011/0050225 A1    3/2011  Prisner
2015/0097561 A1*  4/2015  Desmulliez ............ G01N 22/00
                                              324/300

OTHER PUBLICATIONS

Vasyl Denysenkov et al., "Liquid state Dynamic Nuclear . . . ", Journal of Magnetic Resonance 217 (2012) 1-5.
C. J. R. Sheppard, "Approximate calculation . . . ", Pure Appl. Opt. 4 (1995) 665-669.
J. Bart et al., "Optimization of stripline-based . . . ", Journal of Magnetic Resonance 201 (2009) 175-185.
Jerzy Krupka et al., "High Q-factor Microwave . . . ", IEEE Transactions on Ultrasonics, Ferroelectrics, and Frequency Control, vol. 52, No. 9, Sep. 2005.
R.N. Clarke et al., "Fabry-Perot and open . . . ", J.Phys. E:Sci. Instrum, vol. 15, 1982.

\* cited by examiner

Prior Art

MICROWAVE RESONATOR WITH DISTRIBUTED BRAGG REFLECTOR (=DBR)

This application is the national stage of PCT/EP2014/064747 filed on Jul. 9, 2014 and claims Paris convention priority from DE 10 2013 214 930.1 filed Jul. 30, 2013, the entire disclosures of which are hereby incorporated by reference.

BACKGROUND OF THE INVENTION

The invention concerns an NMR (nuclear magnetic resonance) probe head comprising a microwave resonator having at least two elements which are reflective in the microwave range, at least one of which is focusing, wherein the reflective elements at least partly delimit a resonance volume of the microwave resonator.

A configuration of this type is disclosed e.g. in US 2011/0050225 A1 (reference [2]) which describes the use of a Fabry-Pérot resonator (FP) in the field of DNP-NMR/EPR.

A Fabry-Pérot resonator typically consists of two parallel metallic mirrors located opposite each other at a separation L. In quasi-optical systems, one or both mirrors may have a spherical shape (with a radius of curvature $R_i$). The electromagnetic field distribution within such a resonator can be described by the paraxial solution of the Helmholtz equation which is based on Gaussian optics. The resonance frequency of the FP resonator depends on the radii of curvature $R_{1,2}$, the mirror separation L and the desired resonance modes. In the special case of transverse electromagnetic modes $TEM_{mnq}$ a particular mode is unambiguously determined by the indices m, n, and q.

Figure 3:
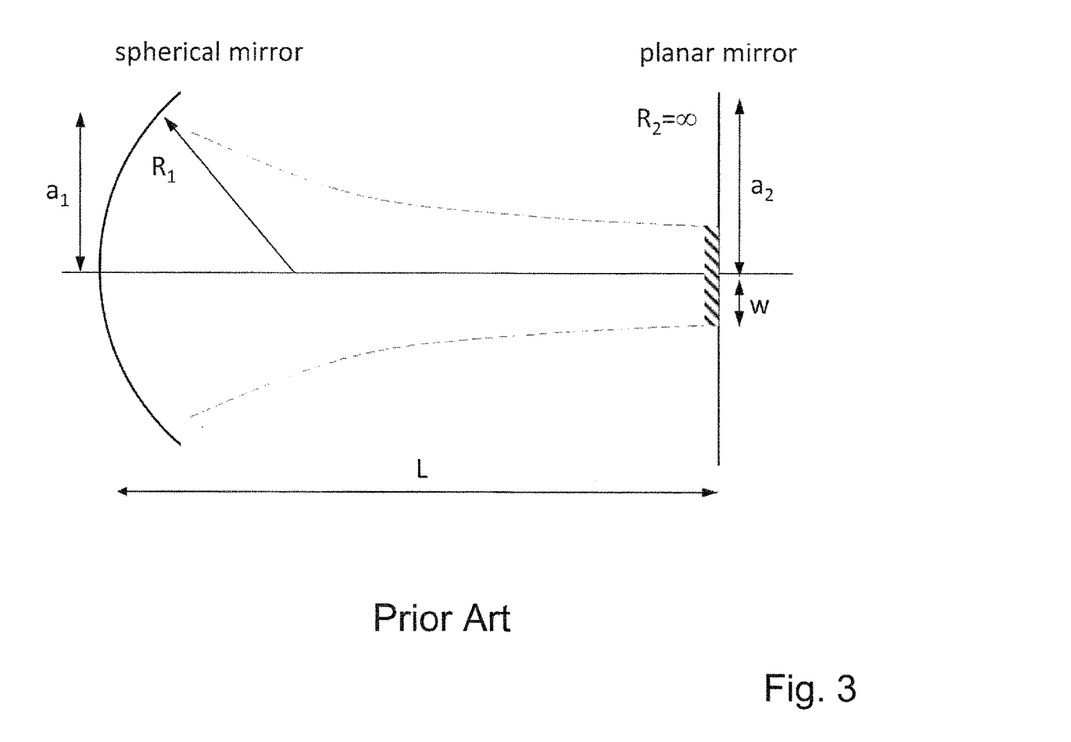
FIG. 3 shows a schematic view of a Fabry-Pérot resonator according to prior art consisting of a spherical and a planar mirror.

One possible implementation of an FP resonator consists of a spherical and a planar mirror in accordance with present FIG. 3, wherein in accordance with reference [1] the resonance frequency is given by $$f_r\left[q + \frac{m+n+1}{\pi}\left(\tan^{-1}\frac{L}{R_1-L}\right)^{\frac{1}{2}}\right]\frac{c}{2L}$$

Figure 2:
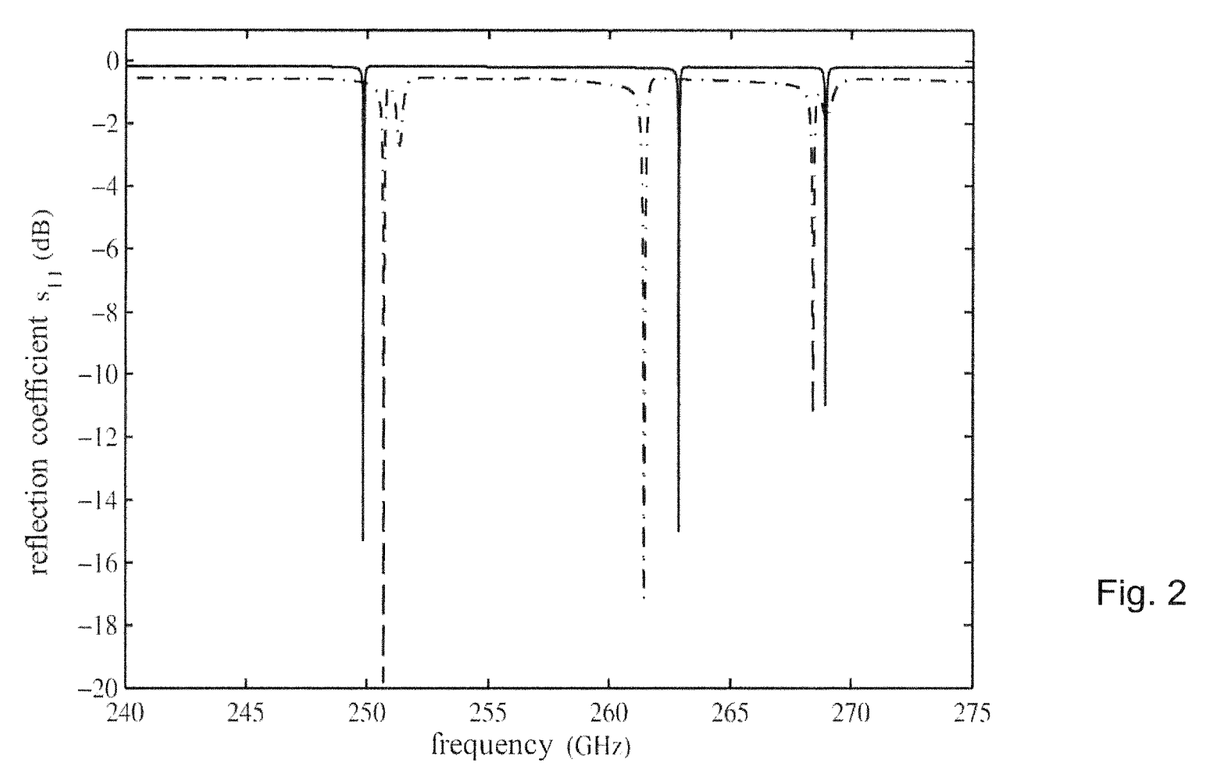
FIG. 2 shows the simulation of an ideal FP resonator with a metallic mirror in comparison with a simulated reflection curve of a model with DBR instead of the metallic mirror.

As is illustrated in the left half of FIG. 2, a mirror element formed as a stack of dielectric layers with different permittivities is also disclosed in optics as an alternative to a metallic mirror. Such a structure is designated as distributed Bragg reflector (DBR) in optical configurations. The reflectivity of a DBR is determined by the number and permittivity of the dielectric layers as $$R = \left[\frac{n_0(n_2)^{2N} - n_s(n_1)^{2N}}{n_0(n_2)^{2N} + n_s(n_1)^{2N}}\right]^2$$

$n_0$, $n_1$, $n_2$, and $n_s$ correspond to the refractive indices of the background material, the alternating layers and the substrate material (cf. e.g. reference [4]).

There are experimental methods in the field of nuclear magnetic resonance spectroscopy which enable a significant increase in the nuclear polarization and therefore in the detection sensitivity of the experiment. One of these methods is dynamic nuclear polarization (DNP). This technology is based on the excitation of electron spins in stable radicals and, due to the gyromagnetic relationship of the electron spin, requires simultaneous irradiation of a magnetic microwave field at a frequency which is higher by a factor of 660 than the nuclear Larmor frequency of the 1H nuclei.

A typical DNP configuration consists of an NMR coil which is tuned to a nuclear Larmor frequency (e.g. $^1$H—400 MHz) and simultaneous irradiation of a microwave field at 263 GHz. DNP configurations are described e.g. in reference [3].

The major problem of the current prior art consists in that the sample should be located as closely as possible to the NMR detection coil while being excited as homogeneously as possible by means of a microwave field. While in the case of an FP resonator homogeneous microwave excitation is easy to realize, the presence of a conductive mirror in the direct vicinity of the sample causes two problems:

1.) The currents induced in the mirror distort the field of the detection coil and reduce the detection sensitivity.

2.) the transition between the metallic mirror and the sample interferes with the external (static) magnetic field, thereby reducing the spectral resolution of the experiment.

Departing therefrom, it is the underlying purpose of the present invention to provide a microwave resonator of the above-mentioned type which enables location of an NMR detection coil as closely as possible to the sample, wherein the distortions of the static field by resonator components are reduced such that the detection sensitivity and the spectral resolution of the experiment are considerably improved.

SUMMARY OF THE INVENTION

This object is achieved in a surprisingly simple fashion with technical means that are readily available by an NMR probe head of the above-mentioned type which is characterized in that at least one of the reflective elements is designed as a DBR (distributed Bragg reflector) and that the NMR probe head comprises at least one NMR coil which is integrated in the DBR.

In this way, a microwave resonator with a considerably increased efficiency is provided, since the use of dielectric layers in a reflective element considerably reduces the losses in comparison with conventionally used metallic layers on a reflective element.

In contrast to the standard FP resonator, the use of a DBR in accordance with the invention allows replacement of a metallic mirror by a dielectric component. This design is particularly useful in order to minimize field distortions caused by the presence of the metallic components:

Distortion of an external static magnetic field caused by the susceptibility of the material used. The advantage consists in that the resonator can be designed such that DNP experiments with higher spectral resolution become possible (cf. e.g. reference [5]). Towards this end, the boundary surfaces between materials of different susceptibility must be positioned parallel to the static magnetic field. In this case, the B0 field in the surrounding volume is not distorted.

Distortion and reduction of an RF field caused by a conductive (metallic) mirror and the accompanying reduction of the RF efficiency (NMR detection sensitivity). As a result, a resonator geometry is realized which offers increased RF field homogeneity and increased RF efficiency.

Only a non-conductive mirror offers the possibility of integrating the RF coil in or on the mirror since the RF coil is then of course not short-circuited. The resulting advantage is the closeness between RF coil and sample.

Moreover, by means of the inventive microwave resonator, channels can be introduced into the dielectric layers which permit exact positioning of the sample in the maximum of the magnetic microwave field.

Integration of the NMR coil in the DBR results in minimum distortion/scattering/diffraction/mode conversion of the microwave field and also in a maximum magnetic RF field amplitude in the sample. Stripline resonators for RF can also be integrated in the DBR in addition to planar geometries.

In one preferred embodiment of the inventive microwave resonator, at least two, in particular all reflective elements are focusing. Focusing achieves an increased field amplitude or energy density at a point in space.

In other preferred alternative embodiments of the invention, one of the reflective elements is focusing and one is planar. The combination of one focusing and one planar element facilitates the geometry, wherein the advantages of focusing are largely maintained. Moreover, planar structures are easier to produce.

In a third alternative variant, one of the reflecting elements is focusing and one is defocusing. This configuration permits (partial) focusing of the microwave field in any spatial areas.

Advantageous further developments of these embodiments are characterized in that the surface of at least one of the focusing and/or defocusing elements has a spherical shape. A spherical shape is particularly easy to produce with conventional production methods.

In one alternative further development, the surface of at least one of the focusing and/or defocusing elements has an elliptical shape. An elliptical shape improves "illumination" of an elongated spatial area. A special application may require a special form of the focusing or defocusing element.

In one particularly preferred embodiment, at least one of the reflective elements has a metallic surface, advantageously a metallic coating. Metallic coatings are easy to produce from a manufacturing point of view, in particular, for focusing or defocusing elements. A coating of different materials perpendicular to the B0 field direction may be advantageous when the resonator is to be operated in a static magnetic field which is as homogeneous as possible.

In another preferred embodiment, the DBR is designed for a wavelength range of 10 cm to 100 μm, preferably of 30 mm to 0.3 mm. This enables selection of a desired mode or definition of the wavelength range relevant for an application. Undesired modes can additionally also be suppressed in this fashion.

In further particularly preferred embodiments of the inventive microwave resonator, the DBR comprises at least five dielectric layers. When exactly 5 dielectric layers (quartz, air) are used, a reflection factor is achieved which is of the order of magnitude of the reflexivity of metal layers.

In another advantageous embodiment of the inventive microwave resonator, a coupling element for microwave radiation is provided on the side of the at least one DBR facing away from the resonance volume of the microwave resonator. Microwave radiation must be coupled into the resonator volume in order to excite the resonator. The geometry of the coupling-in structure determines the so-called resonator Q-factor on which scaling of the energy density in the resonator is based. Lateral coupling-in, e.g. through the partially transmitting DBR, offers the advantage of more efficient coupling compared to classical iris coupling.

The present invention also concerns a nuclear magnetic resonance (NMR) probe head comprising a microwave resonator of the above-described inventive type, which is characterized in that the sample position of the probe head during the measuring operation is located in the resonance volume of the microwave resonator. In comparison with CW excitation, resonators offer the advantage of spatial separation of the maxima of the electric and magnetic fields. The field amplitude is moreover scaled by the resonator Q-factor.

In particularly advantageous embodiments of the inventive NMR probe head, the sample position is located in the minimum of the electric field of the microwave resonator. Under these circumstances, a minimum amount of electrical field energy is dissipated in the sample.

These embodiments can be improved by further developments, in which the NMR probe head comprises at least one NMR coil which induces a magnetic RF (radio frequency) field at the sample position. For this reason, an RF field and a microwave field can simultaneously be generated in the same sample volume in order to excite an MR sample at the respective Larmor frequency of the corresponding nuclei or electrons.

In one variant, the NMR probe head comprises means for supplying the sample to the sample position. A spatially defined position of the sample supply is the prerequisite for minimum disturbance of the microwave field distribution.

One particularly preferred class of embodiments of the inventive NMR probe head is characterized in that the at least one NMR coil integrated in the DBR is disposed on the surface of the DBR. The advantage of such a configuration is the closeness between the NMR coil and the sample volume. Relevant for the field generated by the coil are the sensitivity as well as the field homogeneity, wherein one parameter is generally optimized at the expense of another parameter. Due to the degrees of freedom in two spatial directions, planar NMR coils offer the freedom of realizing almost any geometries within the plane such as e.g. circles, spirals or rectangles. In this way, the balance between sensitivity and homogeneity can be well adapted to the sample volume.

In advantageous further developments of these embodiments, the NMR coil is designed as an RF coil, disposed on the first layer of the multilayer DBR and shaped such that it is transparent to microwave radiation. The RF coil may be shaped either such that its conductor paths do not project at all into the microwave beam path, e.g. in a circular or rectangular embodiment. The conductor paths may furthermore be dimensioned such that their width and separation only minimally affect the microwave beam, such that the major part is still transmitted through the RF coil. This is e.g. the case when the conductor width is considerably smaller than the wavelength and the separation between neighboring conductor paths is considerably larger.

In preferred variants of these further developments, the NMR coil is constructed as a grid. A periodic grid structure can be used to form an RF coil with a plurality of conductor paths, which increases its inductivity and ultimately provides high sensitivity. Although such a grid may be disadvantageous for the propagation of the microwave beam, there are certain values for grid parameters such as conductor width and separation, as already indicated above, for which the transmission can be adjusted in dependence on the polarization of the incident microwave beam such that the majority of the beam is transmitted. There are different scientific documents in this connection, which precisely examine the influence of the grid parameters. A defined variation of the beam profile, e.g. for focusing the beam, with which the grid parameters are varied within the plane in dependence on the location is also possible. This type of optimization can be realized via wave-optical calculation.

In one alternative class of embodiments, the inventive NMR probe head is characterized in that the at least one NMR coil which is integrated in the DBR is designed as an RF coil, that the DBR comprises a plurality of layers and that the NMR coil is disposed on the rear side of the first layer of the DBR facing away from the other reflective element. Advantageous in this case is that the RF coil is no longer in the region of the microwave beam since the major part of this beam has been reflected back by the DBR. Thus, the RF coil can be optimized independently of the microwave beam and, at the same time, the DBR is transparent to the RF coil. The separation between the RF coil and the sample volume has a disadvantageous effect on the sensitivity but an advantageous effect on the field homogeneities, both of the alternating field generated by the coil and on the homogeneity of the static field. The latter provides spectral lines of improved resolution and can therefore nevertheless present the preferred solution in comparison with a coil which is more closely positioned.

In further particularly advantageous embodiments of the inventive NMR probe head, the DBR has a plurality of dielectric layers and channels are provided in the front side, facing the other reflective element, of at least the first layer of the DBR, the channels being structured to exactly spatially position the NMR sample. A defined channel size also allows adjustment of the sample volume. Such a defined sample position and sample size is indispensable for reproducible results. Moreover, a tightly sealed space can be generated for liquid or gaseous samples. The possibility of placing one or a plurality of channels parallel to the field direction of the static magnetic field moreover results in minimum disturbance of the static field, thereby maximizing the spectral resolution. These embodiments can be further developed in that channels are provided in several layers of the DBR for spatial positioning of an NMR sample. This offers the possibility of increasing the sample substance amount that is located in the active area of the sample volume, which results in a higher fill factor and therefore in a higher signal amplitude. As described above, the RF coil geometry can also be adjusted to the sample geometry in order to optimize the sensitivity or homogeneity.

A further class of embodiments of the inventive NMR probe head is characterized in that the NMR probe head is part of an MR spectrometer for performing an EPR, ENDOR or NMR-DNP experiment. In these experiments, a sample is simultaneously exposed to a homogenous RF or microwave field with as high an intensity as possible. The invention combines the advantages of compact NMR coils and an efficient FP resonator.

In an alternative class of particularly compact embodiments, the NMR probe head is part of an apparatus for DNP polarization. DNP results in a signal-amplified NMR spectrum. The invention consists (i) of a geometry which causes minimum distortion of the external magnetic field, (ii) of an efficient NMR coil geometry with high fill factor, and (iii) an efficient microwave resonator in order to excite the electron spin transition with minimum microwave power. The resonance volume extends into the DBR due to the distributed reflection.

A DNP configuration of this type can be produced with an FP in accordance with FIG. 3. In order to correctly position a liquid sample in the RF and microwave field, a channel can be introduced into one of the upper layers of the DBR mirror. Due to the purely dielectric mirror, the NMR coil can be designed as a spiral which is concentric to the sample.

The inventive DBR should, if possible, be designed of a material with a high thermal conductivity and a large permittivity difference between neighboring layers. In this fashion, the dissipated heat can be quickly discharged. The reflectivity of the individual layers increases due to the high permittivity difference.

Further advantages of the invention can be extracted from the description and the drawing. The features mentioned above and below may be used in accordance with the invention either individually or collectively in arbitrary combination. The embodiments shown and described are not to be understood as an exhaustive enumeration but have exemplary character for describing the invention.

The invention is illustrated in the drawing and is explained in more detail with reference to embodiments. In the drawing:

DESCRIPTION OF THE PREFERRED EMBODIMENT

The main application of the invention is in the field of electron resonance spectroscopy (ESR), nuclear magnetic resonance spectroscopy (NMR) and in the field of dynamic nuclear polarization. The invention comprises a sub-THz resonator with a so-called "distributed Bragg reflector" (DBR).

The invention concerns a new system for recording microwave reflection spectra.

Figure 1:
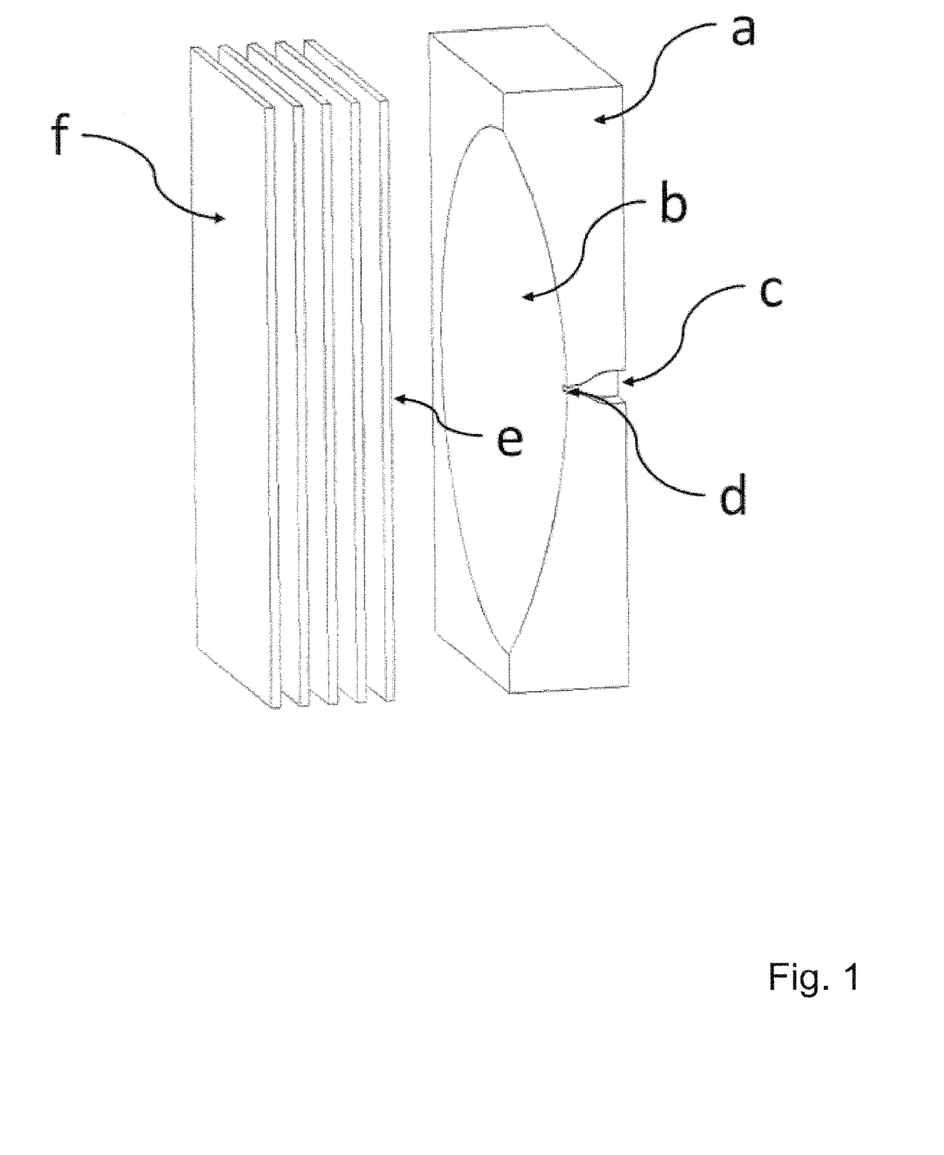
FIG. 1 shows a schematic view of an inventive microwave resonator designed as a Fabry-Pérot resonator, in which a planar metallic mirror is replaced by a DBR.

FIG. 1 shows an inventive microwave resonator in which the planar metallic mirror in an FP resonator was replaced by a DBR:
a—spherical mirror body,
b—spherical mirror with radius of curvature $R_1$,
c—microwave supply,
d—iris coupling,
e—resonant volume and sample location,
f—distributed Bragg reflector.

In order to clearly illustrate the inventive principle, a comparative study with two geometries was performed:

A first model consisted of an ideal FP resonator with a metallic mirror, a second model consisted of a DBR.

The simulated reflection curve ($s_{11}$ parameter) is illustrated in FIG. 2. The same spherical mirror was used in both cases.

FIG. 2 shows in detail:
(Continuous line) a simulated s11 parameter for an FP resonator with $R_1$=10 mm, $\Delta$=2.95 mm and a $TEM_{005}$ resonance at 263 GHz;
(Dashed line) the same simulation with a 5-layer DBR ($\varepsilon_{r1}$=3.75, $\varepsilon_{r2}$=1).

In both cases, the $TEM_{005}$ resonance occurs at the same frequency. The coupling iris was not changed in the simulation, which indicates a similar resonance Q-factor. The invention is therefore particularly suited as a resonator for DNP experiments.

The present invention comprises i.a. the following aspects:

1. A Fabry-Pérot resonator with a metallic and a distributed Bragg reflector for magnetic resonance experiments.
2. A DBR consisting of a stack of planar, curved, non-metallic plates with a refractive index of ≠1.
3. An optimized DBR with internal channels in order to position an NMR/EPR or NMR/DNP sample.
4. A DBR with internal or external coil which were optimized for optimum detection of the NMR signal or for generating defined field gradients.
5. A DBR which is designed such that distortions of the static field in the sample volume are minimized, either through selection of suitable materials, through a special geometry, or through a combination of both.
6. A DBR which can be used as an adjustable coupler in order to couple-in a microwave/THz beam into the FP resonator.

FIG. 3 shows a Fabry-Pérot resonator according to prior art consisting of a combination of a spherical and a planar mirror with a high reflectivity. A flat liquid EPR/DNP sample can be placed directly on the surface of the planar mirror where the electric microwave field is small.

Figure 4:
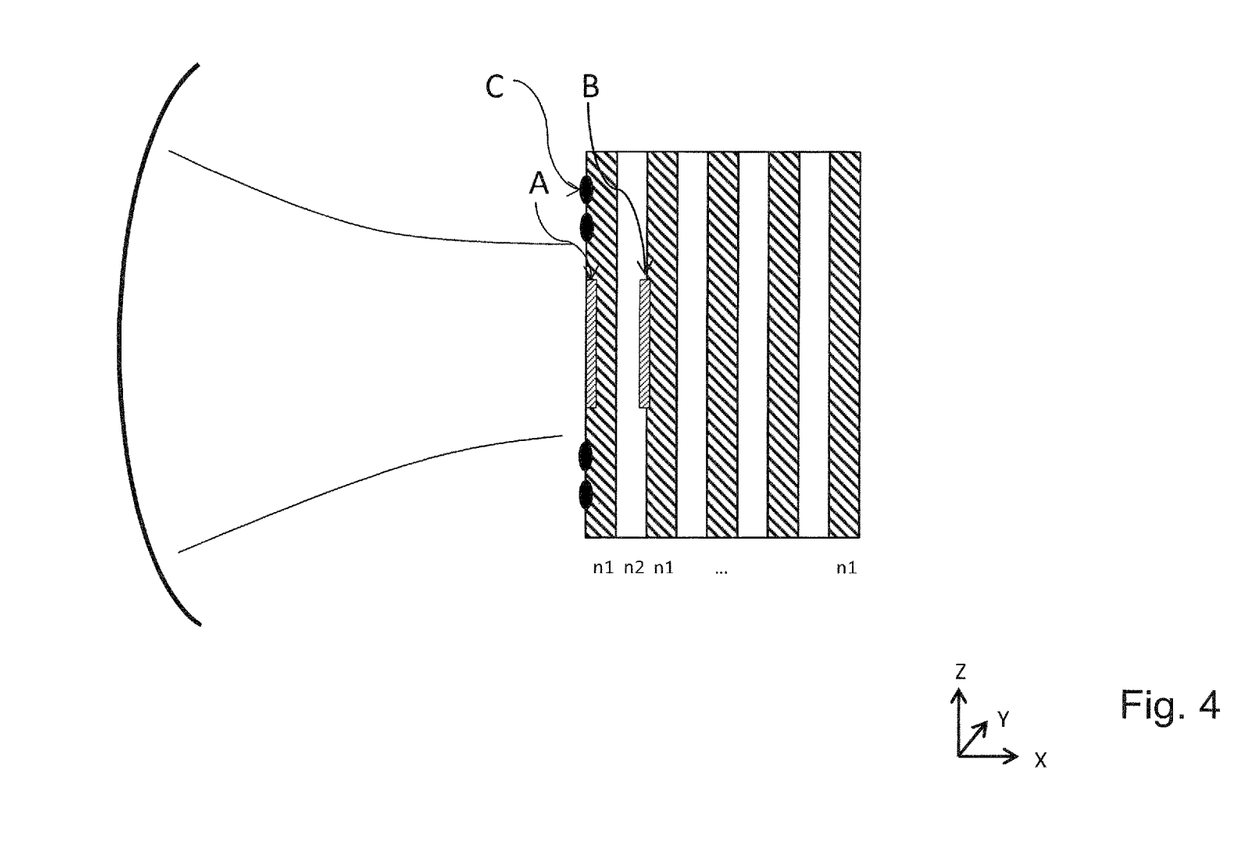
FIG. 4 shows a schematic view of a Fabry-Pérot resonator consisting of a spherical mirror and a DBR in which sample channels and an RF coil are integrated.

FIG. 4 shows, by way of example, an inventive Fabry-Pérot resonator consisting of a spherical mirror (thick curved line) and a DBR consisting of layers with alternating refractive indices $n_1$ and $n_2$ (hatched and white rectangles). The microwave beam is illustrated by enveloping lines at the same field amplitude (thin curved lines). The sample channels (A) and (B) are introduced into the DBR. The conductor paths of the RF coil (C) are located on the side facing the mirror.

Figure 5:
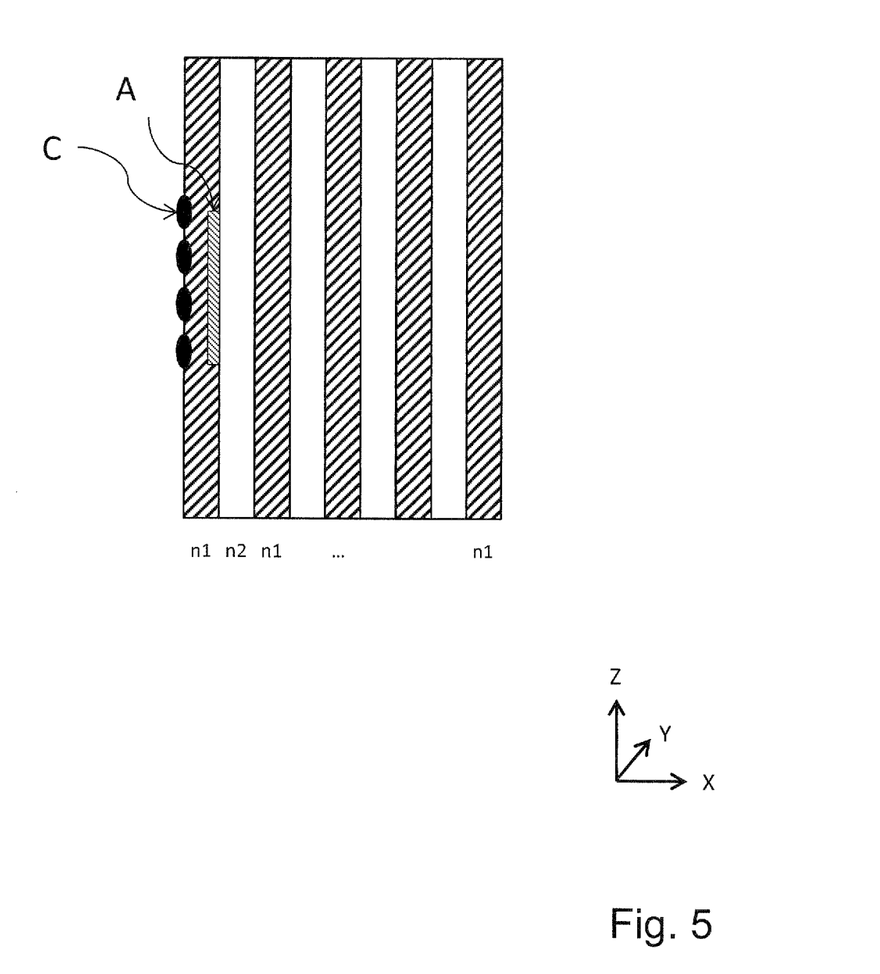
FIG. 5 shows a schematic view of a DBR in which a sample channel and an RF coil are integrated on the side facing the reflective element.

In contrast to the view of FIG. 4, FIG. 5 shows a DBR with a sample channel (A) and an RF coil (C), the conductor paths of which are located within the microwave beam (not shown). Through suitable selection of conductor width and separation, the majority of the microwave power can also be transmitted through the RF coil in this case.

Figure 6:
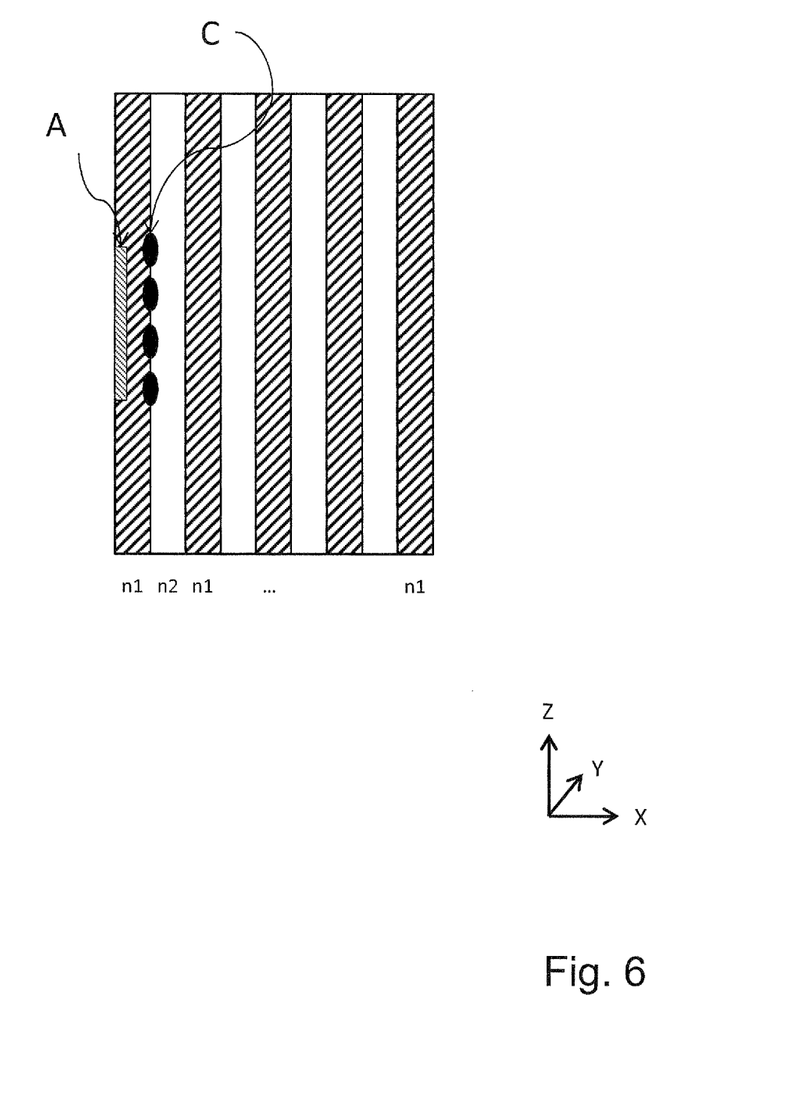
FIG. 6 shows a schematic view of a DBR in which a sample channel and an RF coil are integrated between the layers of the DBR.

In contrast to the view of FIG. 5, FIG. 6 shows a DBR into which a sample channel (A) was introduced directly on the side facing the spherical mirror. The RF coil (C) is introduced between the layers of the DBR.

ABBREVIATIONS

ESR electron spin resonance
(N)MR (nuclear) magnetic resonance
DNP dynamic nuclear polarization
MAS magic angle spinning
DBR distributed Bragg reflector
FP Fabry-Pérot resonator
PBS photonic band-gap structure
hrNMR high resolution NMR
RF in NMR spectroscopy the electromagnetic frequency range from 1 MHz to 1000 MHz
Microwave electromagnetic frequency range between 1-300 GHz
THz tera hertz, electromagnetic frequency range of 0.3-3 THz

EXPLANATION OF TERMS

| | |
|---|---|
| Fill factor | the ratio between field-filled space and sample volume; weighted with the field amplitude |
| Q-factor | ratio between the EM energy stored in the resonator and the energy which is converted during a frequency period through (material) losses or radiation |

LIST OF REFERENCES

[1] H. Kondo et al.:
"Millimeter and Submillimeter Wave Quasi-Optical Oscillator with Multi Elements", IEEE Trans. Microw. Theory Techn. 40 (5) (1992) 857-863

[2] V. Denysenkov, Th. Prisner:
EP 2 269 045 B1; US 2011/0050225 A1

[3] V. Denysenkov, Th. Prisner:
"Liquid state Dynamic Nuclear Polarization probe with Fabry Perot resonator at 9.2 T", J. Magn. Reson. 217 (2012), 1-5

[4] C. J. R. Sheppard:
"Approximate calculation of the reflection coefficient from a stratified medium", Pure and Applied Optics: Journal of the European Optical Society Part A. 4, Nr. 5, 1995

[5] J. Bart, J. W. G. Janssen, P. J. M. van Bentum, A. P. M. Kentgens, J. G. E. Gardeniers:
"Optimization of stripline-based microfluidic chips for high-resolution NMR", J. Magn. Reson. 201 (2009) 175-185

The invention claimed is:

1. An NMR (nuclear magnetic resonance) probe head, the probe head comprising:
a microwave resonator having at least two reflective elements which are reflective in the microwave range, wherein at least one of said two reflective elements is focusing, said at least two reflective elements at least partly delimiting a resonance volume of the microwave resonator, wherein at least one of said at least two reflective elements is a DBR (distributed Bragg reflector); and
at least one NMR coil which is integrated in said DBR.

2. The NMR probe head of claim 1, wherein at least two reflective elements are focusing.

3. The NMR probe head of claim 1, wherein all reflective elements are focusing.

4. The NMR probe head of claim 1, wherein one reflective element is focusing and one is planar.

5. The NMR probe head of claim 1, wherein one reflective element is focusing and one is defocusing.

6. The NMR probe head of claim 1, wherein a surface of at least one of said reflective elements has a spherical or elliptical shape.

7. The NMR probe head of claim 1, further comprising a coupling element for microwave radiation disposed on a side of said DBR facing away from said resonance volume of said microwave resonator.

8. The NMR probe head of claim 1, wherein a sample position of the probe head is disposed in said resonance volume.

9. The NMR probe head of claim 1, wherein a sample position of the probe head is disposed at a minimum of an electric field of said microwave resonator during measuring operation.

10. The NMR probe head of claim 8, wherein the NMR probe head comprises at least one NMR coil which induces a magnetic RF (radio frequency) field at the sample position.

11. The NMR probe head of claim 10, wherein the NMR probe head further comprises an element for supplying a sample to the sample position.

12. The NMR probe head of claim 1, wherein said at least one NMR coil which is integrated in said DBR is disposed on a surface of said DBR.

13. The NMR probe head of claim 12, wherein said DBR has a plurality of layers and said NMR coil is designed as an RF coil, wherein said NMR coil is disposed on a first layer of said DBR and is transparent to microwave radiation.

14. The NMR probe head of claim 13, wherein said NMR coil is designed as a grid.

15. The NMR probe head of claim 1, wherein said at least one NMR coil is designed as an RF coil and said DBR has a plurality of layers, wherein said NMR coil is disposed on a rear side, facing away from an other reflective element, of a first layer of said DBR.

16. The NMR probe head of claim 1, wherein said DBR comprises a plurality of dielectric layers and channels are provided in a front side, facing an other reflective element, of at least a first layer of said DBR, said channels enabling exact spatial positioning of an NMR sample.

17. The NMR probe head of claim 16, wherein channels are provided in a plurality of layers of said DBR for spatially positioning an NMR sample.

* * * * *